United States Patent [19]

Torzala

[11] 4,295,475
[45] Oct. 20, 1981

[54] PROBE AND SYSTEM FOR DETECTING PROBE DISLODGEMENT

[75] Inventor: Terence A. Torzala, Warminster, Pa.
[73] Assignee: Air Shields, Inc., Hatboro, Pa.
[21] Appl. No.: 88,474
[22] Filed: Oct. 26, 1979
[51] Int. Cl.³ .............................................. A61B 5/00
[52] U.S. Cl. .............................. 128/736; 73/343 R; 200/61.02; 200/DIG. 36; 340/600
[58] Field of Search ................ 128/1 B, 630, 639–641, 128/643, 644, 653, 664–667, 736, 687–690, 303.13, 908; 340/531, 555, 556, 573, 600; 200/61.02, DIG. 36; 73/343 R, 344

[56] References Cited

U.S. PATENT DOCUMENTS

| | | | |
|---|---|---|---|
| 2,737,644 | 3/1956 | Krieger | 340/600 |
| 2,976,419 | 3/1961 | Menke et al. | 340/600 X |
| 3,300,770 | 1/1967 | Broussea et al. | 340/600 X |
| 3,329,946 | 7/1967 | Robbins | 340/600 X |
| 3,569,710 | 3/1971 | Jalink | 340/600 X |
| 3,930,249 | 12/1975 | Steck et al. | 340/600 X |
| 4,164,937 | 8/1979 | Spencer | 128/688 X |

FOREIGN PATENT DOCUMENTS 2730574  2/1978  Fed. Rep. of Germany ...... 128/736

*Primary Examiner*—Lee S. Cohen
*Attorney, Agent, or Firm*—Weiser, Stapler & Spivak

[57] ABSTRACT

A contact probe arranged to detect dislodgement of the probe from a body to which it has been attached. Probe dislodgement is detected by sensing an increased radiation level falling on a main sensor (14) located in the contact surface (10a) of the probe. The main sensor cooperates with a reference sensor (16) located in another surface (10b) of the probe which receives radiation reflected from the skin of the body to which the probe is attached. The reference sensor (16) provides a floating reference for the main sensor (14). In addition to providing an indication of probe dislodgement, the two sensors cooperate to develop an indication when they are shielded from the radiation source, thereby rendering the probe inoperative to sense probe dislodgement.

13 Claims, 2 Drawing Figures

PROBE AND SYSTEM FOR DETECTING PROBE DISLODGEMENT

DESCRIPTION

1. Technical Field

The present invention relates, in general, to probes and, in particular, to a contact probe arranged for detecting dislodgement of the probe from a body to which it has been attached and apparatus for providing an indication of such dislodgement. Although the invention will be described in connection with a body temperature sensing probe, it will be apparent that the invention has broader application.

2. Background Art

Many probes are in use today to measure or monitor a function of the body to which the probe is attached or to control or influence a body state or condition. For example, the thermal environment of an infant incubator may be regulated by sensing the body temperature of the infant and developing a signal, representative of the infant's body temperature, for controlling the incubator heater. In such an application, it is important that intimate contact, between the skin and the probe contact surface which carries the temperature sensor, be established and maintained. Should the probe become dislodged, resulting in a total or partial loss of contact, the heater will respond to a temperature measurement other than the infant's body temperature.

One approach, currently in use, for detecting probe dislodgement involves using information directly from the function being monitored. A significant deviation in the measurement of a body function may be the result of a significant change in the body function itself or the result of the measuring probe being dislodged from the body. In either case, an indication of the condition should be developed. While such an approach may be adequate for certain applications to sense a complete dislodgement of the probe, a partial dislodgement may produce an inadequate deviation and go unnoticed. Also, in some applications, the function being monitored may not change so appreciably upon probe dislodgement as to produce an adequate indication. For example, in an incubator, the ambient temperature is approximately equal to the temperature of the infant. Therefore, when a probe attached to the infant becomes dislodged and exposed to the thermal environment of the incubator, there may be very little, if any, immediate change in the output of the temperature sensor.

Another technique which has been suggested for detecting probe dislodgement involves sensing impedance changes due to changing contact conditions between the probe and the body. This approach has met with only limited acceptance. It has been found that various other factors besides loss of contact between the probe and the body affect the impedance. As a result, this technique does not provide adequate reliability.

U.S. patent application Ser. No. 075,253 filed on Sept. 13, 1979 by Benjamin L. Hochman discloses another approach for detecting probe dislodgement. The apparatus disclosed in this Hochman application senses an increased level of radiation impinging upon the body contact surface of the probe when the probe is dislodged from the body. Although this general technique is extremely useful in effectively detecting probe dislodgement, the particular apparatus disclosed in the Hochman application has certain limitations. The probe in the Hochman patent application is arranged to operate with respect to a fixed threshold. As a result, variations in the ambient conditions may cause false alarms if the threshold is set too low or partial probe dislodgement may go undetected if the threshold is set too high to protect against false alarms.

DISCLOSURE OF INVENTION

Accordingly, it is an object of the present invention to provide a new and improved probe.

It is another object of the present invention to probe a probe arranged for detecting dislodgement of the probe from a body to which it has been attached.

It is a further object of the present invention to provide apparatus which develops an indication when a probe is dislodged from a body to which it has been attached.

It is yet another object of the present invention to provide a probe which is reliable in operation, relatively simple in construction, and may be fabricated at reasonable cost.

A probe, constructed in accordance with the present invention, includes a probe housing having a contact surface adapted for contact with a body and a second surface adapted to be spaced from the body and upon which radiation reflected from the body impinges when the contact surface is in contact with the body. First radiation receiving means are located in the contact surface of the housing for sensing an increased radiation level impinging on the contact surface when the probe housing is dislodged from the body and the contact surface is exposed to the increased radiation level. The first radiation receiving means develop an output representative of the increased radiation level. Second radiation receiving means are located in the second surface of the housing for sensing radiation reflected from the body and for determining when a decreased level of radiation impinges upon the second surface as happens when the probe is covered. The second radiation receiving means develop an output representative of the decreased radiation level. Emanating from the probe housing are means for transmitting to a remote location the outputs of the first and second radiation receiving means.

An additional aspect of the present invention is the alarm circuitry which, in response to the outputs of the first and second radiation receiving means, develops an indication when these two outputs have a particular relationship signifying probe dislodgement or that the probe is inoperative because it is shielded from the radiation source.

BRIEF DESCRIPTION OF DRAWINGS

Referring to the drawing.

BEST MODE OF CARRYING OUT THE INVENTION

Figure 1:
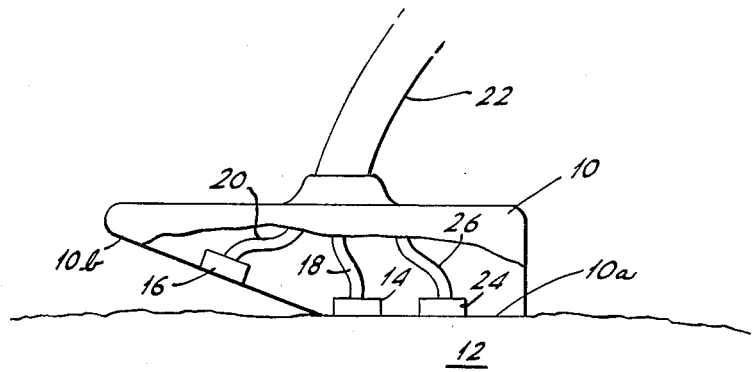
FIG. 1 is a side view, partially cut away, showing a preferred embodiment of the probe constructed in accordance with the present invention.

Referring to FIG. 1, a probe, constructed in accordance with the present invention, includes a housing 10 having a contact surface 10a adapted for contact with a body 12. The probe has a second surface 10b adapted to be spaced from body 12 and upon which radiation reflected from body 12 impinges when contact surface 10a is in contact with body 12. For the embodiment of the invention illustrated in FIG. 1, the included angle between surface 10b and contact surface 10a is approximately 160°.

Also included in a probe constructed in accordance with the present invention are first radiation receiving means, located in contact surface 10a, for sensing an increased radiation level impinging on the contact surface when the probe is dislodged from body 12 and the contact surface is exposed to the increased radiation level. The radiation receiving means may include a photo-conductor 14 which develops an electrical signal representative of the light level received by the photo-conductor. Photo-conductor 14 may be of the cadmium sulfide type which has a spectral response closely matching that of the human eye and, therefore, ideally suited for sensing light from tungsten and fluorescent lights having radiation characteristics concentrated in the visible electromagnetic radiation range. The resistance value of photo-conductor 14 is dependent upon the amount of light falling upon the photo-conductor. When no light falls upon the photo-conductor, the resistance is very large. When exposed to light the resistance of the photo-conductor is much smaller. Accordingly, the voltage drop across photo-conductor 14 is representative of the light level impinging upon contact surface 10a.

The FIG. 1 probe further includes a second radiation receiving means, located in surface 10b, for sensing radiation reflected from body 12. The second radiation receiving means may include, like the first radiation receiving means, a photo-conductor 16, again of the cadmium sulfide type, which develops an electrical signal representative of the light level received by this photo-conductor.

Emanating from the probe housing of FIG. 1 are means for transmitting to a remote location the outputs from the first and second radiation receiving means. In particular, lead wire pairs 18 and 20 conduct the signals developed by photo-conductors 14 and 16, respectively, to the alarm circuitry which will be described below. The lead wire pairs form part of a cable 22 which emanates from the top surface of housing 10.

Also located in contact surface 10a is a sensor 24 for measuring or monitoring a body function. Sensor 24 may be a thermistor which develops an electrical signal representative of the temperature of body 12. The thermistor signal is conducted to a remote location via a lead wire pair 26 which may form a part of cable 22, as shown, if the temperature signal is to be transmitted to the same remote location as the light signals carried on lead wire pairs 18 and 20. The thermistor signal may be used merely to provide a temperature measurement indication or it may serve, for example, to control an incubator heater to effect a desired thermal environment in an incubator.

As shown in FIG. 1, when the probe is disposed against body 12, little, if any, radiation (ambient light for the example being described) impinges on contact surface 10a of the probe housing. As a result, photo-conductor 14 receives little, if any, light. At the same time, photo-conductor 16 receives radiation (ambient light for the example being described) reflected from the surface of body 12. The resistance ratio of photo-conductors 14 and 16 for this condition establishes the threshold for the alarm circuitry of FIG. 2.

Figure 2:
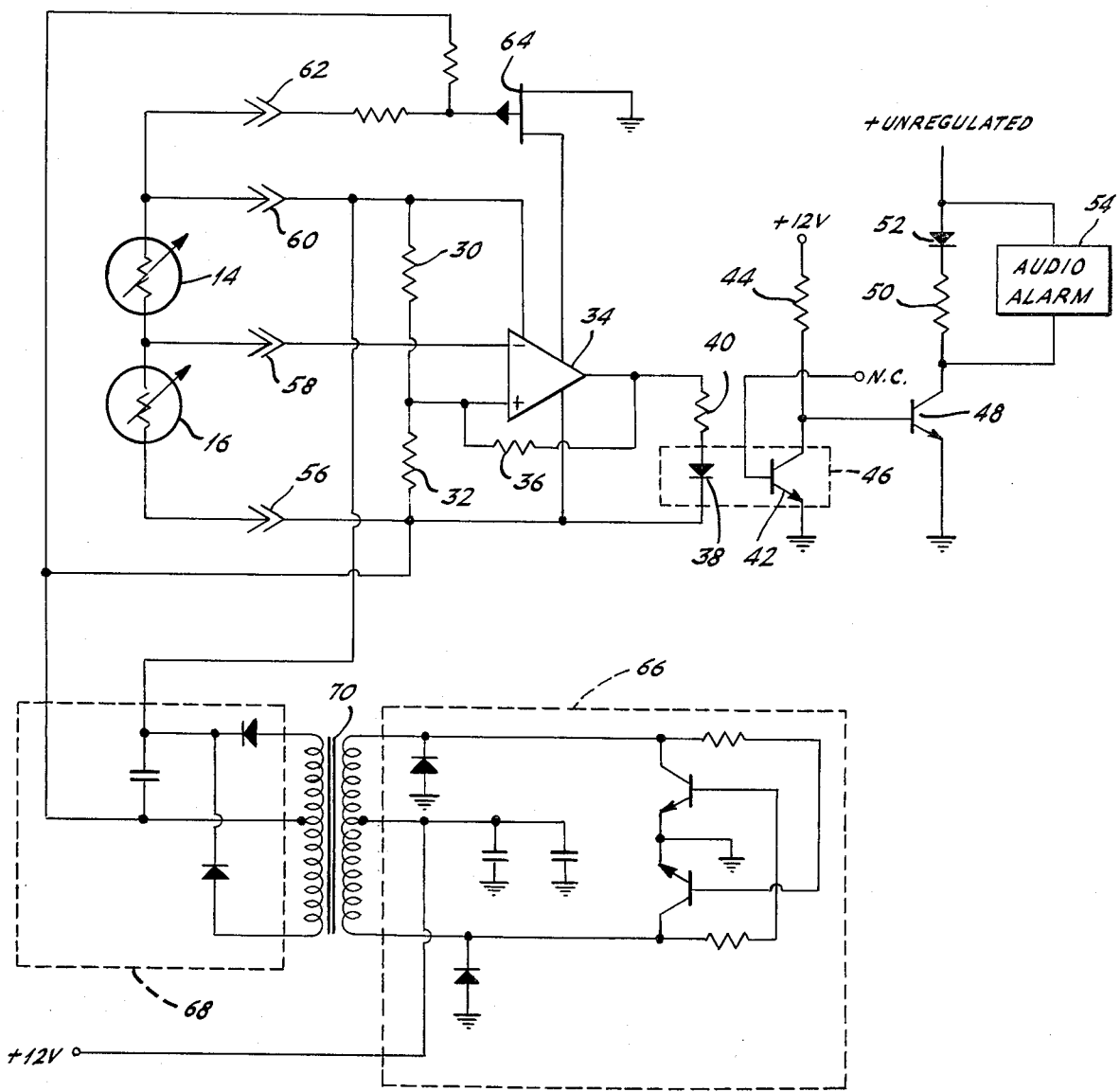
FIG. 2 is a schematic diagram of a circuit which may be used with the FIG. 1 probe to develop an indication of probe dislodgement.

Not shown in FIG. 1 are the means for holding the probe in place on body 12. Such means may include, a tape, belt or strap or other like member. If the probe works loose from its intimate contact with body 12 to result in either a partial or complete dislodgement, photo-conductor 14 senses an increased light level impinging on contact surface 10a. This reduces the resistance ratio of photo-conductor 14 and 16 to a value below the threshold and the alarm circuitry of FIG. 2 is arranged to provide an indication when this condition exists. When the probe becomes covered by a blanket or by the means which hold it in place on the body, photo-conductor 16 senses a decreased light level impinging on surface 10b. This also reduces the resistance ratio of photo-conductors 14 and 16 to a value below the threshold and again the alarm circuitry of FIG. 2 will provide an indication when this condition exists. Thus, the arrangement of photo-conductors 14 and 16 is such that photo-conductor 16, responsive to changes in the ambient conditions, provides a floating reference for photo-conductor 14 to detect probe dislodgement even when the ambient conditions change and also senses when the system becomes inoperative because the probe is shielded from the ambient light.

Referring to FIG. 2, photo-conductors 14 and 16 of the probe are arranged on one side of a bridge circuit and a pair of resistors 30 and 32 are arranged on the other side of the bridge circuit. A high input impedance operational amplifier 34 is connected across the bridge circuit, with the negative input terminal of the amplifier connected to the junction of photo-conductors 14 and 16 and the positive input terminal of the amplifier connected to the junction of resistors 30 and 32. A feedback resistor 36 is connected between the output of amplifier 34 and its positive input terminal. The values of resistors 30, 32 and 36 are selected so that resistors 30 and 36 each are much larger than resistor 32. As a result, the inputs to amplifier 34 are:

$$V_D = \frac{R_{16}}{R_{14} + R_{16}} V_S \qquad (1)$$

$$V_R = \frac{R_{32}}{R_{32} + R_{30}} V_S + \frac{R_{32}}{R_{32} + R_{36}} V_O \qquad (2)$$

where $V_D$ is the voltage applied to the negative input terminal of amplifier 34

$V_R$ is the voltage applied to the positive input terminal of amplifier 34

$V_O$ is the output voltage of amplifier 34

$V_S$ is the supply voltage applied at the junction of photo-conductor 14 and resistor 30.

The voltage drops across photo-conductors 14 and 16, being determined by the ratio of the resistance values of the photo-conductors, represent the relative light levels impinging upon the photo-conductors. When contact surface 10a of the probe is in intimate contact with body 12, only that portion of the ambient light which is transmitted through the body tissue plus a small amount of light penetrating under the probe impinge upon photo-conductor 14. During this condition the resistance value of photo-conductor 14 is high. At the same time, photo-conductor 16 receives ambient light reflected from body 12 and its resistance value is considerably lower than that of photo-conductor 14. Thus, input voltage $V_D$ is very small. Input voltage $V_R$ is greater than input voltage $V_D$ when contact surface 10a of the probe is in intimate contact with body 12 and the resistance value of photo-conductor 14 is high. This causes the output voltage $V_O$ of amplifier 34 to rise to a positive level slightly below the supply voltage and corresponds to a normal operating condition.

When the contact surface 10a of the probe becomes dislodged from body 12, additional ambient light impinges upon photo-conductor 14. Even a partial dislodgement causes such a drop in the resistance value of photo-conductor 14 as to develop at the junction of photo-conductors 14 and 16 an input voltage $V_D$ to amplifier 34 which is greater than input voltage $V_R$. This causes the output voltage $V_O$ of amplifier 34 to drop to zero and corresponds to an alarm condition.

When the probe becomes covered so that photo-conductor 16 is shielded from ambient light, the resistance value of photo-conductor 16 rises in response to the decreased amount of light impinging upon this photo-conductor. The voltage developed at the junction of photo-conductors 14 and 16 again is greater than the input voltage $V_R$ causing the output voltage $V_O$ of amplifier 34 to drop to zero. This again corresponds to the alarm condition.

Thus, when the voltage drops across photo-conductors 14 and 16 have a predetermined relationship such that input voltage $V_D$ is greater than input voltage $V_R$, the output voltage $V_O$ of amplifier 34 drops to zero signifying either probe dislodgement or probe covering. As an example, the present invention has been implemented by the selection of photo-conductors and other components which are arranged to sense an alarm condition whenever the resistance ratio for photo-conductors 14 and 16 is 10:1 or less. While contact surface 10a is in contact with body 12, the resistance of photo-conductor 14 is in the order of 87 million ohms. So long as the probe remains uncovered and photo-conductor 16 receives light reflected from body 12, the resistance of this photo-conductor is in the order of 10,000 ohms. The resistance ratio of the two photo-conductors for this condition of the probe is well in excess of 10:1 and corresponds to normal operation. The foregoing assumes no significant change in the ambient light conditions. To the extent that the ambient light level rises or falls slightly, the resistance ratio of photo-conductors 14 and 16 does not change appreciably and remains in excess of 10:1.

Upon partial dislodgement of the probe from body 12, the resistance of photo-conductor 14 drops to a much smaller value, such as less than 100,000 ohms. This drops the resistance ratio of photo-conductors 14 and 16 to below 10:1 and changes the relative voltage drops across photo-conductors 14 and 16 such that input voltage $V_D$ rises to a level adequate to cause the output voltage $V_O$ of the amplifier to drop to zero.

When the probe becomes covered or there is a complete loss in ambient light, the resistance of photo-conductor 16 rises to a much higher value, such as more than 8.7 million ohms. This also drops the resistance ratio of photo-conductors 14 and 16 to below 10:1 and changes the relative voltage drops across photo-conductors 14 and 16 from normal operation such that input voltage $V_D$ rises to a level adequate to cause the output voltage $V_O$ of the amplifier to drop to zero.

If the probe is dislodged from body 12 while it is covered or during a period of complete loss of ambient light, both photo-conductors are exposed to the same light conditions. As a result, the resistance ratio of the photo-conductors is approximately 1:1 and the level of input voltage $V_D$ again is adequate to cause the output voltage $V_O$ of the amplifier to drop to zero.

The output voltage $V_O$ of amplifier 34 is coupled to a light emitting diode 38 through a resistor 40. When the output voltage $V_O$ is high (contact surface 10a is in contact with body 12 and the probe is not covered), light emitting diode 38 radiates. When the output voltage $V_O$ is zero (contact surface 10a is dislodged from body 12 or the probe is covered), light emitting diode 38 ceases to radiate.

Cooperating with light emitting diode 38 is a phototransistor 42 having its emitter connected to ground, its collector connected to a +12 V source through a resistor 44, and its base floating. Phototransistor 42 is in proximity to light emitting diode 38 to sense when the light emitting diode radiates or ceases to radiate. The dashed box, identified by reference numeral 46, represents the proximity of light emitting diode 38 to phototransistor 42.

The collector of phototransistor 42 is connected to the base of a transistor 48 which has its emitter grounded and its collector connected to a positive supply voltage through a resistor 50 and a light emitting diode 52. Phototransistor 42 controls the operation of transistor 48. When phototransistor 42 senses radiation from light emitting diode 38 (contact surface 10a is in contact with body 12 and the probe is not covered), transistor 48 is biased to cut-off and light emitting diode 52 remains turned off. When phototransistor 42 does not sense radiation from light emitting diode 38 (contact surface 10a is dislodged from body 12 or the probe is covered), transistor 48 is turned on and light emitting diode 52 radiates to indicate an alarm. An audible alarm 54 is shown connected in parallel with resistor 50 and light emitting diode 52.

Reference numerals 56, 58, 60 and 62 represent the connections from the probe photo-conductors 14 and 16 to the alarm circuitry. If any of the lead wires from the probe become disconnected, the output voltage $V_O$ of amplifier 34 will drop to zero corresponding to the alarm condition. When lead wire 56 becomes disconnected, input voltage $V_D$ to the negative input terminal of amplifier 34 rises to the supply voltage $V_S$. With input voltage $V_D$ greater than input voltage $V_R$, the output voltage $V_O$ of the amplifier becomes zero.

When lead wire 58 becomes disconnected, there is no path for bias current of the negative input terminal of amplifier 34. The effect is to apply the supply voltage $V_S$ to the negative input terminal of amplifier 34. Again, with this input to the amplifier greater than input voltage $V_R$, the output voltage $V_O$ of the amplifier becomes zero.

When either lead wire 60 or lead wire 62 becomes disconnected, the voltage at the junction of photo-conductor 14 and resistor 30 drops to zero removing the supply voltage from the gate of a junction field effect transistor 64. This causes junction field effect transistor 64 to conduct and thereby apply a signal to amplifier 34 inhibiting the amplifier. The output voltage $V_O$ of the amplifier again becomes zero.

The remaining portions of the FIG. 2 circuitry are fairly standard and, therefore, will be described only briefly. Reference numerals 66 and 68 apply, respectively, to an oscillator and rectifier which are coupled together by a transformer 70 to form a dc-to-dc converter which develops the supply voltage $V_S$. The arrangement is such that body 12, when contacted by the probe, is isolated from the line voltage which is a safety requirement for medical equipment of this type.

Although the invention, as described, contemplates the detection of ambient light, detectors which are selectively responsive to only a portion of the light spectrum (e.g. infrared) may be employed and, likewise, the radiation source may be of a more narrow bandwidth.

As previously stated, the present invention has broader application than as a skin contact temperature probe. The invention may be applied to other body surface probes which monitor or control other body functions or to probes which penetrate the body. For example, the dislodgement or partial withdrawal of an intravenous feed needle, designed to have a contact surface, may be detected by incorporating the principles of the present invention.

While the embodiment of the probe illustrated in FIG. 1 shows the use of photo-conductors at the probe surfaces and the transmission of electrical signals from the probe to a remote location, other electro-optical techniques may be employed in practicing the present invention. For example, fiber-optic bundles may be used to pick up the radiation impinging on surfaces 10a and 10b of the probe and to transmit this radiation to the distant alarm circuit at which photo-conductors convert the radiation to electrical signals.

The foregoing has set forth an exemplary and preferred embodiment of the present invention. It will be understood, however, that numerous alternative embodiments will occur to those of ordinary skill in the art without departure from the spirit or scope of the present invention.

What is claimed is:

1. A probe comprising:
   a probe housing having a contact surface adapted for contact with a body and a second surface adapted to be spaced from said body and upon which radiation reflected from said body impinges when said contact surface is in contact with said body;
   first radiation receiving means located in said contact surface for sensing an increased radiation level impinging on said contact surface when said probe housing is dislodged from said body and said contact surface is exposed to said increased radiation level and for developing an output representative of said increased radiation level;
   second radiation receiving means located in said second surface for sensing (1) radiation reflected from said body, and (2) a decreased radiation level impinging on said second surface when said probe housing is covered and said second surface is exposed to said decreased radiation level and for developing an output representative of said decreased radiation level;
   and means emanating from said housing for transmitting said outputs of said first and said second radiation receiving means to a remote location.

2. A probe according to claim 1 wherein said first and said second radiation receiving means sense visable light.

3. A probe according to claim 2 wherein said second surface is inclined relative to said contact surface.

4. A probe according to claim 3 wherein the included angle between said second surface and said contact surface is approximately 160°.

5. A probe according to claim 1 and further including temperature sensor means located in said contact surface for developing an output representative of the temperature of said body and means for transmitting said output from said temperature sensor means to a remote location.

6. Apparatus for indicating the dislodgement of an article from a body surface, said apparatus comprising:
   an article having a contact surface adapted for contact with said body surface and a second surface adapted to be spaced from said body surface and upon which radiation reflected from said body surface impinges when said contact surface is in contact with said body surface;
   first transducer means having a radiation receiving portion located in said contact surface of said article for (1) sensing an increased radiation level impinging on said contact surface when said article is dislodged from said body surface and said contact surface is exposed to said increased radiation level, and (2) developing a first signal representative of the radiation level impinging upon said contact surface;
   second transducer means having a radiation receiving portion located in said second surface of said article for (1) sensing radiation reflected from said body surface, (2) sensing a decreased radiation level impinging upon said second surface when said article is covered and said second surface is exposed to said decreased radiation level, and (3) developing a second signal representative of the radiation level impinging upon said second surface;
   and alarm means responsive to said first and said second signals for developing an indication when said signals have a predetermined relationship.

7. Apparatus according to claim 6 wherein said first transducer means include a first photo-conductor and said second transducer means include a second photo-conductor.

8. Apparatus according to claim 7 wherein the resistance of each of said photo-conductors varies inversely with the amount of light received by the photo-conductor.

9. Apparatus according to claim 8 wherein said alarm means include circuitry responsive to a predetermined ratio of the resistance values of said photo-conductors.

10. Apparatus for sensing a body function comprising:
   a probe having a contact surface adapted for contact with a body and a second surface adapted to be spaced from said body and upon which radiation reflected from said body impinges when said contact surface is in contact with said body;
   sensor means located in said contact surface and responsive to said body function for developing an output representative of said body function;
   first transducer means having a radiation receiving portion located in said contact surface for (1) sensing an increased radiation level impinging upon said contact surface when said probe is dislodged from said body and said contact surface is exposed to said increased radiation level, and (2) developing a first signal representative of the radiation level impinging upon said contact surface;
   second transducer means having a radiation receiving portion located in said second surface for (1) sensing radiation reflected from said body, (2) sensing a decreased radiation level impinging upon said second surface when said probe is covered and said second surface is exposed to said decreased radiation level, and (3) developing a second signal representative of the radiation level impinging upon said second surface;

alarm means responsive to said first and said second signals for developing an indication when said signals have a predetermined relationship;

and means responsive to said sensor means for developing an indication of said body function.

11. Apparatus according to claim 10 wherein said first transducer means include a first photo-conductor and said second transducer means include a second photo-conductor.

12. Apparatus according to claim 11 wherein said first and said second photo-conductors are electrically connected in a bridge circuit and said alarm means respond to the relative voltage drops across said first and said second photo-conductors.

13. Apparatus according to claim 11 wherein said sensor means is a thermistor which develops a signal representative of the temperature of said body.

* * * * *